United States Patent [19]

Ebert

[11] Patent Number: 4,470,121
[45] Date of Patent: Sep. 4, 1984

[54] MULTI-FREQUENCY VIBRATION CONTROLLER USING FLUID-FILLED CANTILEVER BEAM FOR VIBRATION EXCITATION & ABSORBTION

[75] Inventor: Frederick J. Ebert, Elmwood Park, N.J.

[73] Assignee: United Technologies Corporation, Hartford, Conn.

[21] Appl. No.: 293,733

[22] Filed: Aug. 17, 1981

[51] Int. Cl.³ .................. G06F 15/50; G06F 15/31; G05B 15/02; G01G 3/142
[52] U.S. Cl. .................................. 364/508; 364/509; 364/463; 73/570; 73/579; 73/583; 416/500; 188/322.5
[58] Field of Search .................. 364/508, 509, 463; 416/144, 145, 500, 90 A; 73/570, 579, 583, 514, 651, 500; 188/322.5

[56] References Cited

U.S. PATENT DOCUMENTS

| | | | |
|---|---|---|---|
| 2,302,670 | 11/1942 | Buchanan | 73/514 |
| 3,509,971 | 5/1970 | Gerstine et al. | 416/500 |
| 3,540,809 | 10/1970 | Paul et al. | 416/1 |
| 3,701,499 | 10/1972 | Schubert et al. | 244/17.27 |
| 3,758,758 | 9/1973 | Games et al. | 364/508 |
| 3,904,313 | 9/1975 | Bernaerts | 416/20 |
| 3,911,199 | 10/1975 | Fischer | 174/42 |
| 3,990,811 | 11/1976 | Danielson | 416/20 R |
| 4,226,554 | 10/1980 | Vandiver et al. | 52/168 |
| 4,366,874 | 1/1983 | Pidoux et al. | 177/25 |
| 4,400,941 | 8/1983 | Rauch | 60/520 |

Primary Examiner—Raulfe B. Zache
Assistant Examiner—Archie E. Williams, Jr.
Attorney, Agent, or Firm—Vernon F. Hauschild

[57] ABSTRACT

A variable frequency vibration controller includes a cantilever beam supported from the vibration prone structure whose vibrations are to be controlled. The cantilever beam has selectively shaped hollow interior portions into which fluid can be selectively injected or withdrawn to vary the total mass of the cantilever beam. The cantilever beam natural frequency is thus tuned to match or selectively mismatch the frequency at which the vibration prone structure is vibrating. Thereby, the beam is used to optimally absorb or excite the vibrations of the structure.

15 Claims, 15 Drawing Figures

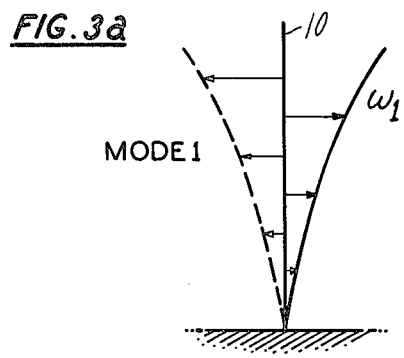
FIG.3a MODE 1
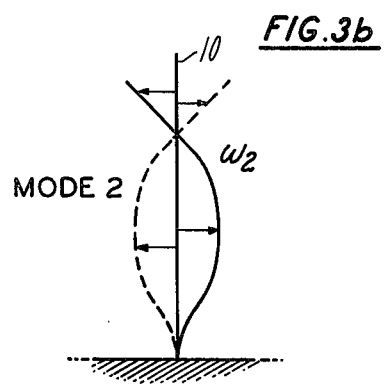
FIG.3b MODE 2
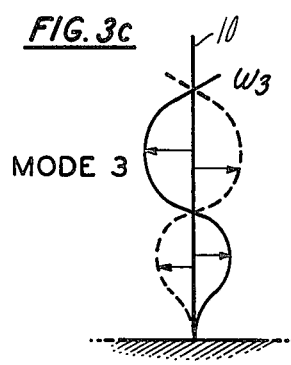
FIG.3c MODE 3
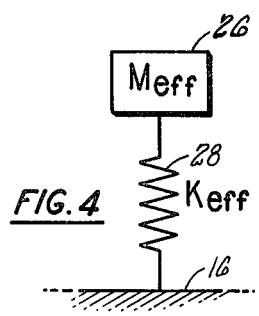
FIG.4

MULTI-FREQUENCY VIBRATION CONTROLLER USING FLUID-FILLED CANTILEVER BEAM FOR VIBRATION EXCITATION & ABSORBTION

DESCRIPTION

1. Technical Field

This invention relates to vibration controller and more particularly to vibration controllers in the form of one or more cantilever beams whose natural frequency can be varied by varying the effective mass thereof by injection or withdrawal of fluid into the cantilever beam hollow interior as a function of the vibrating frequency of the vibration prone structure upon which the cantilever beam is mounted.

2. Background Art

U.S. Pat. No. 3,540,809 of Paul et al, which teaches bifilar vibration absorber mounted on helicopter rotor to absorb the rotor vibrations as a function of rotor RPM before they are transmitted to the passenger or cargo carrying fuselage, and U.S. patent application Ser. No. 185,070 of Mard which utilizes a bifilar absorber fixedly mounted in the helicopter fuselage and tuned as a function of rotor RPM to absorb fuselage vibrations represent the variable frequency vibration absorber art in its present state. These constructions are heavy and mechanically complex.

Another sector of the prior art is represented by Grivolas U.S. Pat. No. 991,717 which teaches a clock pendulum having mercury in its hollow interior, which mercury expands or contracts to compensate for temperature induced variations in the length of the pendulum. However, it will be obvious to those skilled in the art that while the Grivolas device can only change its mass distribution, my device can change its mass as well as its mass distribution. Further, the Grivolas device is only capable of compensating for one type of disturbance, namely temperature, to the frequency it is attempting to hold. My device will compensate for any disturbance to the frequency trying to be held, without respect to how that disturbance is felt or from what that disturbance originates. Still further, the Grivolas mechanism will compensate for frequency disturbance in only one plane, i.e., the plane perpendicular to the clock pendulum weight support wire, whereas, my device will correct for disturbances in any and all planes. Finally, the Grivolas device is a passive system designed to damp out a disturbance, but has no capability for making inputs to the system. Contrary to Grivolas, my device can be passive where my cantilever beam vibration absorber is mounted on a fixed base, but can be an active system when my cantilever device is mounted on a base which can be driven, thereby making the system active so as to effect an input to the system.

DISCLOSURE OF INVENTION

A primary object of the present invention is to provide a lightweight, variable frequency vibration absorber in the form of a cantilever beam whose effective mass, and hence natural frequency, is varied to match the natural frequency of the vibration prone structure to which the cantilever beam is mounted to thereby eliminate or reduce the vibrations of the vibration prone structure.

It is a further object of this invention to teach such a vibration absorber in which the vibrational frequency of the vibration prone structure being controlled is continuously monitored and the effective mass and cross-sectional moment of inertia of the cantilever beam absorber which is mounted therefrom is varied as required to establish the natural frequency of the cantilever beam absorber to match the presently determined frequency of the vibration prone structure for optimum vibration absorption.

It is a further object of this invention to accomplish the cantilever beam vibration absorber natural frequency variation by injecting or withdrawing fluid to the interior of the cantilever beam so as to vary its effective mass and cross-sectional moment of inertia to establish its natural frequency to be equal to the frequency of vibration of the vibration prone structure under control.

It is still a further object of this invention to teach such a cantilever beam vibration absorber in which a plurality of hollow passages are provided within the cantilever beam, and in which the effective mass and hence the natural frequency of the cantilever beam absorber is varied by injecting or withdrawing fluid into one or more of these hollow passages in a manner so that each hollow passage is either completely filled with fluid or completely empty of fluid at all times.

It is still a further object of this invention to teach such a cantilever beam vibration absorber in which the cantilever beam is of cylindrical shape and in which a plurality of small diameter hollow cylindrical tubes, of the hyperdermic needle type, are positioned within the cantilever beam interior so that the axis of the cantilever beam and the axes of the tubes are preferably but not necessarily parallel, and including means to fill or empty selective arrays of these hollow tubes to selectively control the natural frequency of the cantilever beam as a function of the frequency of vibration of the vibration prone structure upon which it is fixedly mounted, and so that the tube array to be fluid filled is selected so that the cantilever beam effective mass is varied to selectively absorb the vibrations of the vibration prone system by establishing cantilever beam vibration at its numerically lowest mode of vibration which will effect vibration absorption.

Other objects and advantages of the present invention may be seen by referring to the following description and claims, read in conjunction with the accompanying drawings.

BRIEF DESCRIPTION OF DRAWINGS

FIGS. 3a, 3b and 3c illustrate the motions of a uniform cantilever beam vibrating in its first, second and third modes of vibration, respectively.

FIG. 4 is a representation of a typical spring suspended mass vibration absorber.

BEST MODE FOR CARRYING OUT THE INVENTION

Figure 1:
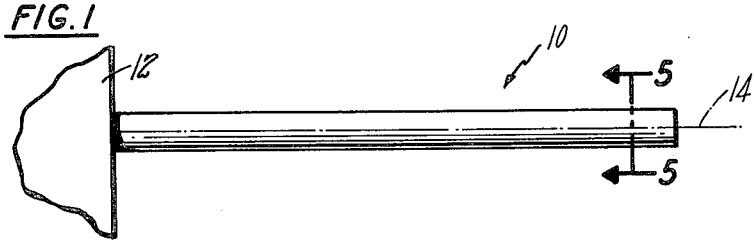
FIG. 1 is a perspective showing of my cantilever beam vibration absorber projecting from the vibration prone support structure whose vibrations are to be controlled thereby.

Referring to FIG. 1 we see my cantilever beam vibration absorber 10 fixedly mounted from vibration prone structure 12 which may be a fixed structure such as a helicopter fuselage, an intermittently movable structure such as a helicopter stabilator, or a continuously movable structure such as a helicopter rotor. While the geometry of cantilever vibration 10 is immaterial, I shall describe it as a cylindrical cantilever beam concentric about axis 14, since this is my preferred embodiment, and will describe its operation in relation to damping vibrations in the fuselage of a helicopter, but it should be borne in mind that this environment is chosen purely for descriptive purposes since it represents one practical environment in which my vibration absorber may be effectively used. My system can also be used to excite vibrations as described hereinafter.

Figure 2:
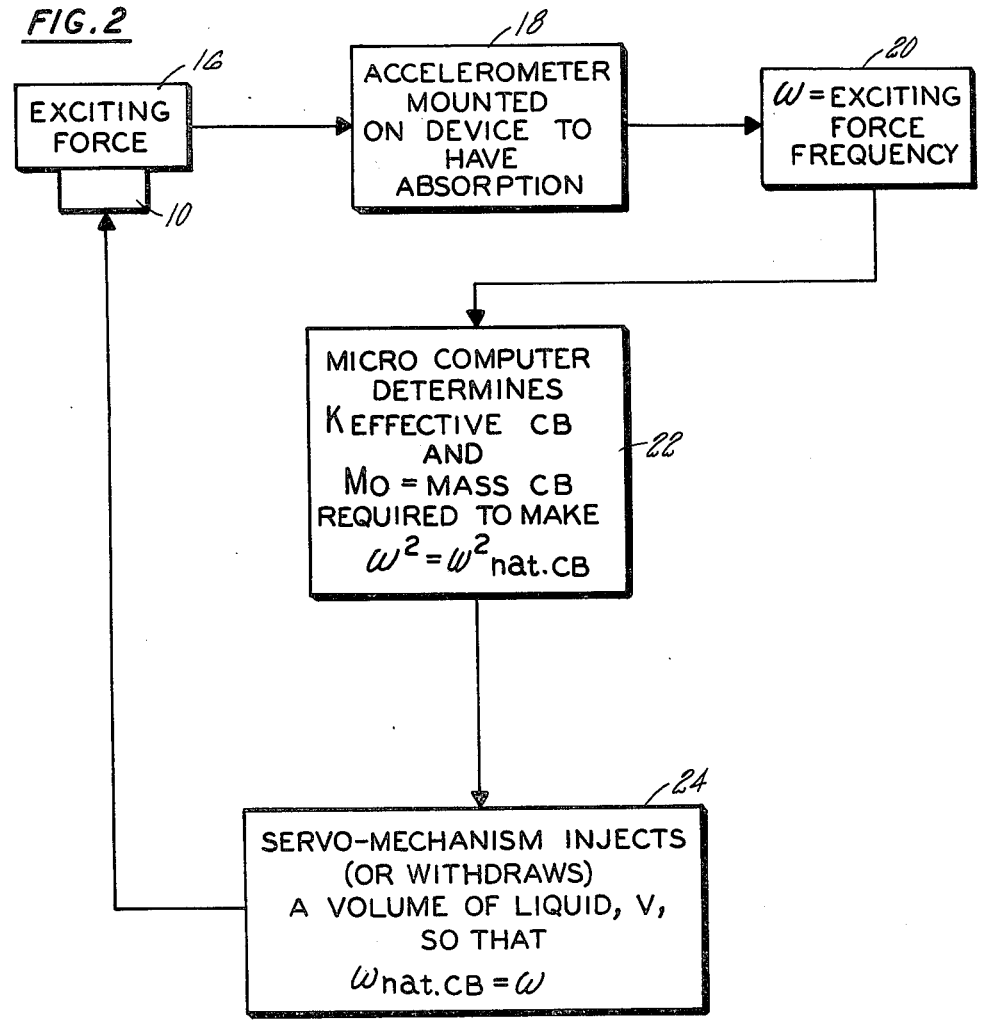
FIG. 2 is a diagrammatic representation of the operation of my variable frequency cantilever beam vibration absorber and its control system.

To best understand the operation of my variable frequency vibration absorber, reference will be made to FIG. 2 which shows a schematic diagram of its operation. In FIG. 2, the vibration prone structure whose vibrations are to be controlled is indicated at 16 and designated as the "exciting force". The vibration prone structure 16 could be a helicopter fuselage which is caused to vibrate by aerodynamic forces imposed thereon by the passage of blades thereover at blade passing frequency. Accelerometer 18, or other appropriate mechanism, is fixedly mounted on the vibration prone structure, such as fuselage 16, and is subjected to the same aerodynamic forces at blade passing frequency. By its nature, accelerometer 18 detects and sends a signal to vibration analyzer 20 which faithfully represents the vibration characteristics in both frequency and amplitude of fuselage 16. Vibration analyzer 20 determines the frequency of vibration $\omega$ of the fuselage and sends a signal of fuselage vibration frequency $\omega$ to the microcomputer 22. Microcomputer 22 is programmed, as described hereinafter, to ascertain the cantiliver beam vibration absorber spring rate $K_{effective\ CB}$ and effective mass $M_o$ required to establish the cantilever beam natural vibration frequency $\omega_{nat.CB}$ to be equal to the determined vibrating frequency $\omega$ of the fuselage. Microcomputer 22 sends to servomechanism 24 signal of $M_o$, the cantilever beam total mass including beam and fluid, required to establish the centilever beam natural frequency to be equal to the present frequency of vibration of the fuselage. Servomechanism 24 either injects or withdraws the proper volume of fluid V into the cantilever beam hollow interior so as to bring its effective mass $M_o$ to that required to establish the desired relationship of having the cantilever beam natural frequency $\omega_{nat.CB}$ equal the vibrating frequency of the fuselage $\omega$. With the cantilever 10 so tuned, it will be caused to vibrate at its natural frequency due to the vibration forces and motions imparted thereto by the vibrating fuselage on which the cantilever beam is mounted. The cantilever beam so vibrating serves to absorb, and therefore either reduce cancel, the vibrations of the fuselage 16 at least in the area of cantilever beam 10. If fuselage 16 is experiencing vibration problems in several areas, several cantilever beam vibration absorbers 10 will be selectively positioned in the vibration problem areas of the fuselage, and also the size and number of cantilever beam vibration absorbers, and their modes of vibration, can be selected as required to produce the force necessary to absorb fuselage vibrations.

In a helicopter, the principal vibration excitation force occurs at blade passage frequency. Accordingly, it is desirable to design the cantilever beam vibration absorber 10 so that it will absorb the excitation force (fuselage vibrations) at blade passage frequency in the cantilever beam absorber's first mode of vibration, although vibration absorption at the second and third modes of vibration would also be helpful. To understand why vibration absorber 10 is most effective when it is designed to perform its vibration absorbing function when vibrating in its first mode of vibration, reference will be made to FIGS. 3a, 3b and 3c which show the first, second and third modes of vibration of cantilever beam 10, respectively. When we consider that the vibration absorbing force F generated by the vibrating cantilever beam 10 can be determined by the equation $F=MA$, where M is the mass of the cantilever beam, and A is its acceleration, it will be noted by viewing FIG. 3a that when cantilever beam 10 vibrates in its first mode of vibration equidistance on opposite sides of its static position illustrated at 10, all mass increments along the length of the cantilever beam 10 are moving in the same direction at all times, and therefore the force being generated at the first mode of vibration can be determined by adding the force generated by each of these cantilever beam mass increments. By comparison, and noting FIG. 3B which shows the vibration absorber space in its second mode of vibration, it will be noted by viewing its fixed line of position, or its phantom line of position, that there are mass increments moving in opposite directions at any given time as illustrated by the arrows and therefore the force generated by these oppositely moving mass increments must be subtracted to produce the total force F generated by cantilever beam 10 in this second mode of vibration. Now viewing FIG. 3c, it will be noted that when cantilever beam 10 is operating in its third mode of vibration, that the mass increments therealong are travelling in opposite directions at any given time and therefore must be subtracted one from the other in determining the total force generated by the cantilever beam when operating in its third mode of operation. It will therefore be seen that maximum vibration absorbing force F can be generated by cantilever beam 10 when vibrating in its first mode of operation, and it will therefore be the objective of my invention to so utilize cantilever beam 10. Further, first mode vibrations decay more slowly than do second and third mode vibrations.

To provide a better understanding of the operation of my cantilever beam vibration absorber and the significance of the FIG. 2 schematic diagram, an explanation of the mathematics involved in the dynamics of absorber 10 will now be given.

From Euler's differential equation governing free vibrations of a cantilever beam, we can derive the following equations:

$$\text{COSH}(\beta \, l)\text{COS}(\beta \, l) = -1, \qquad \text{Eq. 1}$$

where $\text{COSH} \, \beta \, l$ is the hyperbolic cosine of the international constant $\beta$ and the length of the cantilever beam l, and $\text{COS} \, \beta \, l$ is the cosine of the product of the international constant $\beta$ and the length of the cantilever beam l, and $$\omega_{nat.CB} = \beta_n^2 \sqrt{\frac{EI}{m_o}} \qquad \text{Equation 2}$$

where $\omega_{nat.CB}$ is the natural frequency of the cantilever beam, $\beta$ is an international constant, E is the modulus of elasticity of the cantilever beam, I is the cross-sectional area moment of inertia of the cantilever beam, $m_o$ is the distributive mass, i.e., mass per unit length of the cantilever beam and l is the length of the cantilever beam. The total mass of the cantilever beam, $M_o$, equals the product $m_o \, l$.

Equation 2 is the recognized equation for a uniform cantilever beam.

To best understand the operation of the computer 22 in the FIG. 2 schematic and in particular its determination of $K_{eff.CB}$, the effective spring rate of the cantilever beam, and $m_o$, the required cantilever beam distributive mass to establish the cantilever beam natural frequency $\omega_{nat.CB}$ to be equal to the exciting force frequency $\omega$, the above Equations 1 and 2 will be explored further.

While a cantilever beam, such as 10, vibrates in its first mode of vibration as shown in FIG. 3a, its operation can be likened to the conventional spring mounted mass vibration absorber shown in FIG. 4 in which mass 26, having an effective mass of $m_{eff.}$, is suspended from spring 28, having an effective spring rate of $K_{eff.}$, which is in turn suspended from the vibration prone structure 16.

The frequency of vibration of the FIG. 4 spring mounted mass vibration absorber can be expressed:

$$\omega_{eff.} = \sqrt{\frac{K_{eff.}}{m_{eff.}}} \qquad \text{Equation 4}$$

$$\omega_{eff.}^2 = \frac{K_{eff.}}{m_{eff.}} \qquad \text{Equation 5}$$

Now reverting to the uniform cantilever beam Equation 2, and bringing the $\beta_n^2$ quantity within the square root sign, we can rewrite Equation 2 as:

$$\omega_{nat.CB} = \sqrt{\frac{\beta_n^4 \, EI}{m_o}}, \text{ and} \qquad \text{Equation 6}$$

$$\omega_{nat.CB}^2 = \frac{\beta_n^4 \, EI}{m_o} \qquad \text{Equation 7}$$

Comparing Equations 4 and 6, we obtain:

$$\omega_{eff.} = \omega_{nat.CB} \qquad \text{Equation 8}$$

and substituting from Equations 4 and 6, we obtain $$\frac{K_{eff.}}{m_{eff.}} = \frac{\beta_n^4 \, EI}{m_o} \qquad \text{Equation 9}$$

But, since we want $m_{eff.}$ to equal $M_o$, our equation becomes $$K_{eff.} = \beta_n^4 EI \, l \qquad \text{Eq. 10}$$

Utilizing Equations 6 and 10, computer 22 determines quantities $K_{eff.CB}$, the effective spring rate of the cantilever beam, and $M_o$, the cantilever beam total mass required to produce the desired cantilever beam natural frequency to be equal to the natural frequency of the exciting force $\omega$.

Equations 6 or 7 may be used to produce Table I given below:

| n | $(\beta_n \, l)^2$ | $(\beta_n \, l)$ | $W_n / W_1$ |
|---|---|---|---|
| 1 | 3.52 | 1.88 | 1 |
| 2 | 22.03 | 4.69 | 6.26 |
| 3 | 61.70 | 7.85 | 17.53 |
| 4 | 121.40 | 11.02 | 34.49 |
| 5 | 229.86 | 15.16 | 65.30 |
| 6 | 302.99 | 17.41 | 86.08 |
| 7 | 356.32 | 18.88 | 101.23 |
| 8 | 415.72 | 20.39 | 118.10 |
| 9 | 469.26 | 21.66 | 133.31 |
| 10 | 872.78 | 29.54 | 247.95 |
| 11 | 1084.99 | 32.94 | 308.24 |
| 12 | 1283.10 | 35.82 | 364.52 |
| and so forth... | | | |

Wherein n is the cantilever beam natural frequency mode of vibration, $\beta_n$ is an international constant, l is the length of the cantilever beam, $\omega_n$ is the natural frequency of the cantilever beam in mode of vibration n, and $\omega_1$ is the natural frequency of the cantilever beam in the first mode vibration.

Microcomputer 22 of FIG. 2 can be programmed to solve Equation 2 to determine $m_o$ necessary to establish the cantilever beam natural frequency to be equal to $\omega$, the vibrating frequency of the vibration prone structure as determined by the vibration analyzer 20. Column 3 of Table I can be used to determined $\beta_n$, since the length l of the particular cantilever beam vibration absorber being utilized is known. For example, if we wish to have vibration absorber 10 operating at its first mode of vibration principally, we extract the first entry "1.88" from the third column of Table I headed $\beta_n l$, and divide that quantity by the cantilever beam length l properly dimensioned to determine $\beta_n$ required to be entered into Equation 2 to produce first mode vibrations in the cantilever beam vibration absorber. Accordingly, Table I can be used to determine the $\beta_n$ entry to Equation 2 and Equation 2 may be solved to determine the mass $M_o$ of the cantilever beam required to have the cantilever beam 10 vibrate with its first mode of vibration equal to $\omega$, the output of vibration analyzer 20. $M_o$ is the total mass of cantilever beam 10, i.e., the mass of the basic cantilever beam plus the mass of fluid which must be added thereto, or extracted therefrom, to produce the desired $M_o$.

Microcomputer 22 can accordingly be programmed to solve for $m_o$, based upon Equation 2, with the $\beta_n$ input so obtained from Table I, and to also solve for $M_o$.

Figure 5:
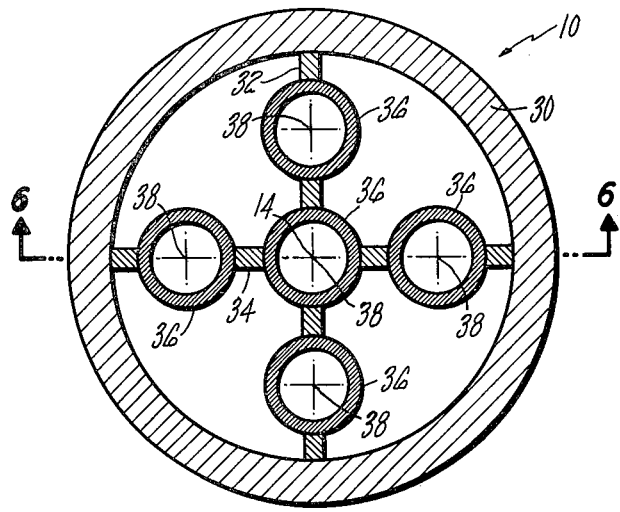
FIG. 5 is an enlarged cross-sectional showing taken along line 5—5 of FIG. 1.
Figure 6:
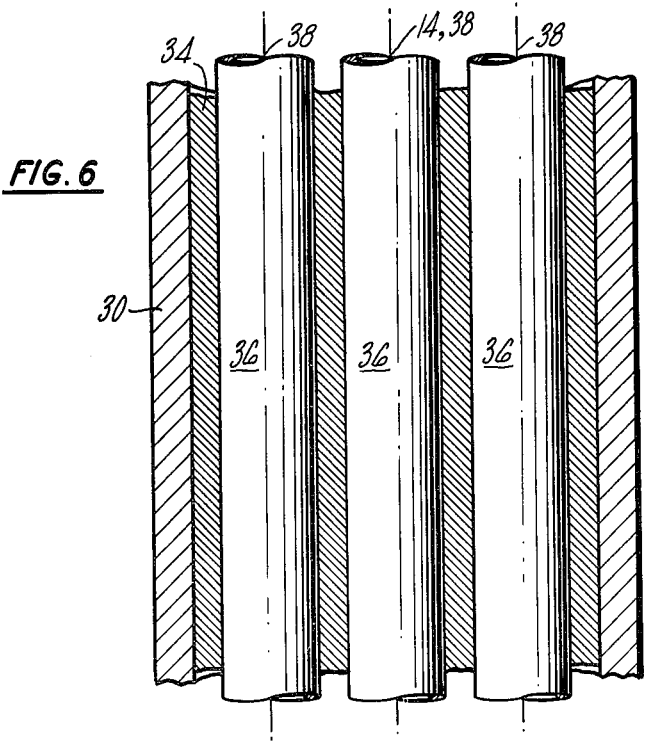
FIG. 6 is a cross-sectional showing along line 6—6 of FIG. 5.

A possible construction of my cantilever beam 10, which is preferably cylindrical in shape but not necessarily so, may be best understood by viewing FIGS. 5 and 6. Cantilever beam 10 may be a solid cylinder, with cylindrical, axial passages drilled therein or, as shown in FIGS. 5 and 6, may be a hollow cylinder comprising outer cylindrical wall 30, which is concentric about axis 14 and carries supported therein by partition members 32 and 34 a plurality of hollow, cylindrically shaped tube members, five of which are shown and identified as 36. Interior tubes 36 are hollow in construction and, may or may not be of the same diameter and length, but are preferably oriented so that their axes 38 extend parallel to axis 14 of cantilever beam 10. While five interior hollow tubes or cylinders 36 are shown in FIGS. 5 and 6, it will be evident to those skilled in the art that any selected array of interior tubes 36 could be chosen. Hollow tubes 36 may be the dimension of a hyperdermic needle, or larger.

It will be evident by viewing FIGS. 5 and 6 that with a five interior tube arrangement, the mass $M_o$ of vibration absorber 10 can be varied substantially between the maximum mass condition when all tubes 36 are filled with the heaviest available fluid, to the minimum mass condition when all tubes 36 are emptied of fluid. It is important in the operation of this vibration absorber 10 that each tube 36 be either totally filled or totally empty of fluid during operation so that a sloshing fluid action is not experienced. It will be evident that any number of interior tubes 36 can be inserted into the interior of vibration absorber 10 thereby increasing the number of tube arrays which can be filled or emptied to vary the tuning of the vibration absorber 10. Further, depending upon the specific problem, an array might be chosen wherein mass is concentrated circumferentially around the outside of the vibration absorber 10 by filling the outermost tubes only, or more mass may be concentrated on the inside of vibration absorber 10 by filling only the tube or tubes at or adjacent to its axis 14.

Figure 7:
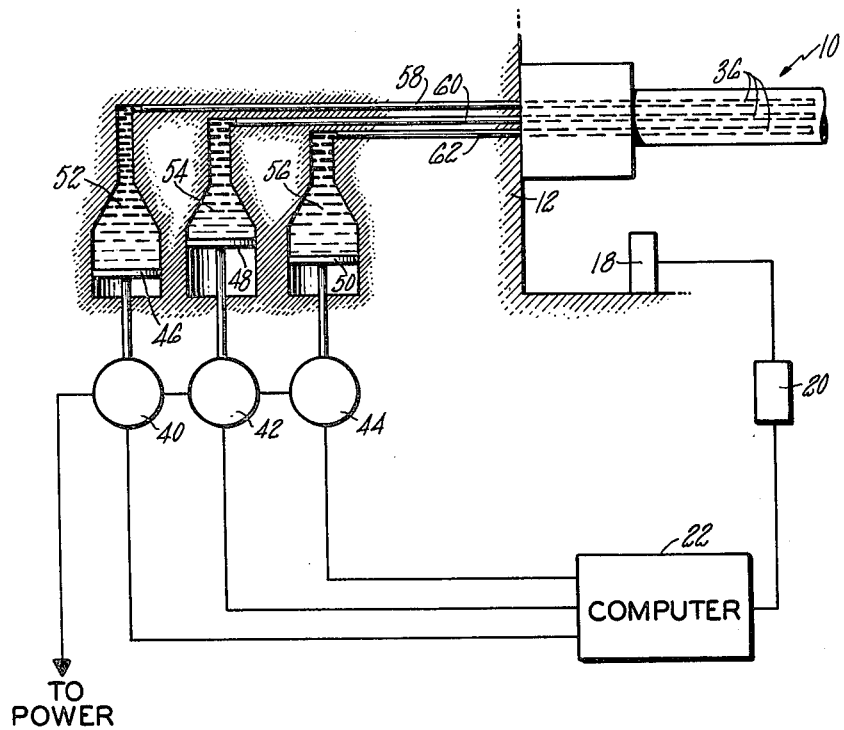
FIG. 7 is a representation of one possible embodiment of my variable frequency cantilever beam vibration absorber system.

A possible embodiment of my invention is shown in FIG. 7 in which cantilever beam vibration absorber 10 is fixedly mounted from vibration prone structure 12, whose vibrations are to be controlled, and accelerometer 18 is similarly mounted thereto. As in the FIG. 2 diagram, the accelerometer 18 faithfully transmits data on the vibration presently being experienced by the vibration prone structure 12, which may be the helicopter fuselage, and transmits that data to the vibration analyzer 20, which calculates the exciting force frequency $\omega$. This $\omega$ signal is transmitted to computer 22, and the required $K_{effective\ CB}$ and $m_o$, and hence $M_o$, are determined by computer 22 so that $\omega_{nat.CB}$ is equal to exciting force frequency $\omega$, and a signal is sent from computer 22 to servomechanisms 40, 42 and 44 as to what volume of fluid V must be injected into or withdrawn from cantilever beam 10 to produce the desired $m_o$ and hence $\omega_{nat.CB}$. Servomechanisms 40, 42 and 44 operate to actuate piston mechanisms 46, 48 and 50 such that they move through fluid reservoirs 52, 54 and 56 so as to either inject or withdraw the required volume of fluid V into cantilever beam 10 through lines 58, 60 and 62, which are connected to cantilever beam interior tubes 36.

Figure 8:
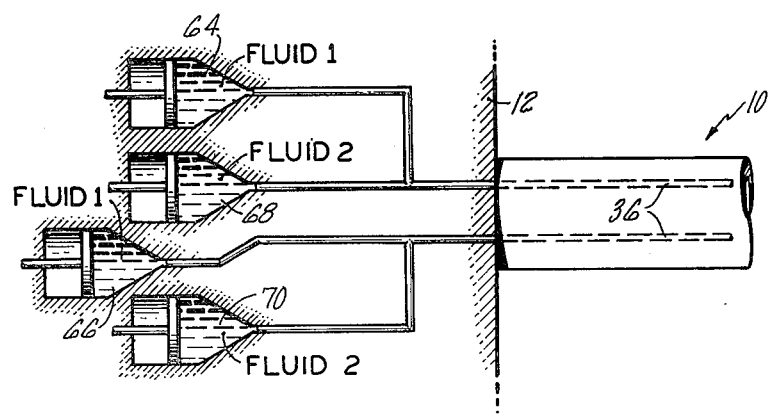
FIG. 8 is a partial showing of my variable frequency cantilever beam vibration absorber system utilizing at least two types of fluid to provide a greater variety of natural frequencies of vibration to which the cantilever beam vibration absorber can be changed.

A portion of a second potential embodiment is shown in FIG. 8, and it should be borne in mind that the FIG. 8 embodiment is similar to the FIG. 7 embodiment in that it includes the accelerometer, vibration analyzer, computer and servomechanisms illustrated in FIG. 7 but not shown in FIG. 8. In the FIG. 8 configuration, the range of natural frequencies to which cantilever beam vibration absorber 10 may be tuned is increased by providing at least two different types of fluid which may be injected into or withdrawn from cantilever beam interior tubes 36. As best shown in FIG. 8, a first fluid is contained in servo operated fluid reservoirs 64 and 66 and a second fluid is contained in servo operated reservoirs 68 and 70.

Reservoirs 64 through 70 are joined through appropriate plumbing to interior tubes 36 so that all tubes 36 may be empty, may be filled with fluid 2, may be filled with fluid 1, or some interior tubes 36 may be filled with fluid 1 while the others are selectively filled with fluid 2 or empty, thereby providing a great variety of cantilever beam total masses $M_o$, and hence a great variety of available cantilever beam natural frequencies $\omega_{nat.CB}$.

Figure 9:
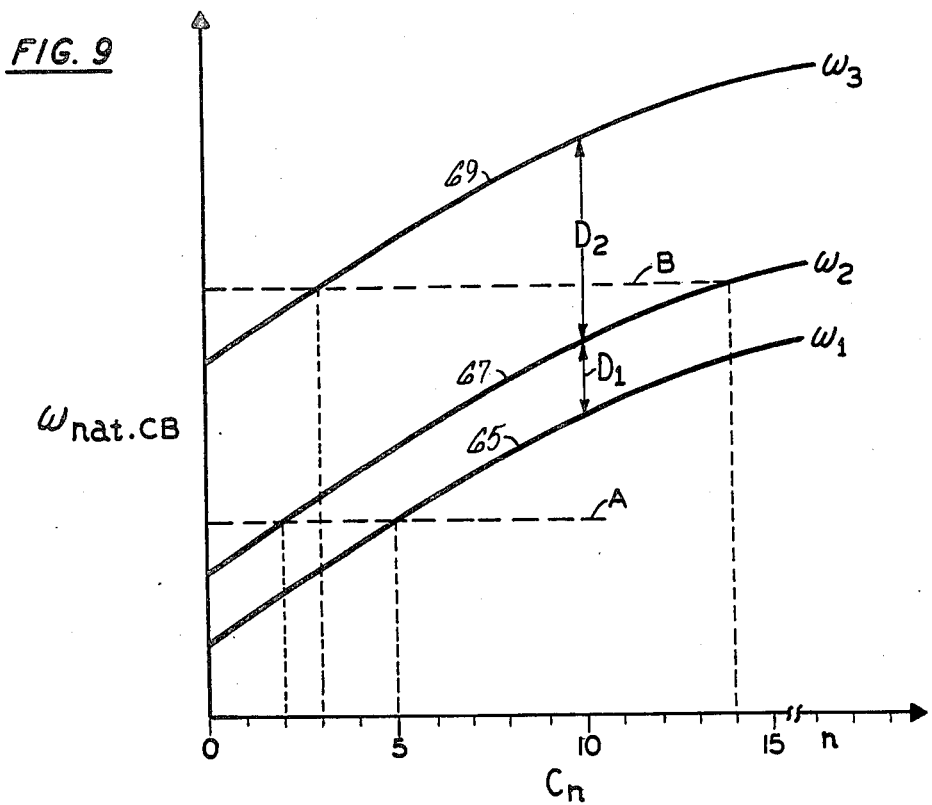
FIG. 9 is a graph of vibration absorber natural frequency plotted against the number of cantilever beam vibration absorber configurations available for fluid injection or extraction to illustrate the choices of configuration available to produce a particular cantilever beam natural frequency vibration.

Computer 22 in any of the above-described configurations may be programmed in accordance with the graph shown in FIG. 9 in which the abscissa indicates the number of interior tube configurations available, $C_n$, the ordinate represents the cantilever beam natural frequency $\omega_{nat.CB}$. Using Equation 2, curves 65, 67 and 69, representing the first, second and third modes of vibration of cantilever beam vibration absorber 10 for each of the configurations $C_n$, can be plotted. In configuration 0, all interior tubes 36 are full of fluid. In viewing the FIG. 9 chart, it will be noted that if our objective is to have the cantilever beam vibration absorber natural frequency $\omega_{nat.CB}$ to be A, this may be achieved by utilizing either tube configurations 5 at the first mode of vibration $\omega_1$, or tube configuration 2 at the second mode of vibration $\omega_2$. Since, as explained earlier, the first mode of vibration is the more durable mode and produces the greater vibration absorbing force, the computer 22 will be programmed to choose tube configuration number 5. It should be noted that while the lowest possible mode is desirable from a force point of view, the higher the mode, the less travel the beam actually experiences. Thus if there are physical size constraints placed on the cantilever beam vibration absorber, it may be necessary to have the beam operate in a configuration which produces $\omega_m$ not $\omega_n$ (m>n) to avoid damaging adjacent aircraft parts. The computer shall be so programmed to provide the lowest vibrational mode provided that the ensuing beam travel does not collide with other parts of the system. Similarly, if we wanted a cantilever beam natural frequency of vibration $\omega_{nat.CB}$ to be $\beta$, it will be noted that this can be achieved with tube configuration 14 using the second mode of vibration $\omega_2$, or with tube configuration 3 using the third mode of vibration $\omega_3$. Because the second mode of vibration produces stronger vibration absorbing forces and does not decay as rapidly as the third mode of vibration, the computer will be programmed to select configuration 14 to utilize the second mode of vibration.

It will be evident that computer 22 can be programmed in accordance with the graph shown in FIG. 9 to produce the desired interior tube 36 configuration $C_n$ which is most desirable to optimally achieve a cantilever beam natural frequency $\omega_{nat.CB}$ equal to the determined present frequency $\omega$ of the vibration prone structure under vibration control by absorber 10.

Figure 10:
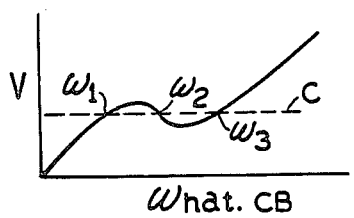
FIG. 10 is a graph of the volume of fluid present at any time in my cantilever beam vibration absorber plotted against the natural frequency of the cantilever beam absorber containing such volume of fluid.

In practice, after a cantilever beam is designed in accordance with my teachings herein, the cantilever beam should be tested using various types of fluid in the interior tubes 36 to ascertain which fluid produces minimal change in internal damping results in the cantilever beam vibration absorber 10, and this fluid would preferably be used. Utilizing Equation 2, and knowing the volume of fluid V which has been added to the cantilever beam vibration absorber at any particular time, the vibration absorber natural frequency $\omega_{nat.CB}$ can be determined and the graph shown in FIG. 10 drawn for each such cantilever beam vibration absorber. When a volume V line, such as C, passes through the graph line more than once, this represents the first, second and third modes of vibration $\omega_1$, $\omega_2$, $\omega_3$, respectively. Utilizing the information contained in the FIG. 10 graph, computer 22 can be programmed to provide the appropriate volume of fluid V to the interior tubes 36 of cantilever beam vibration absorber 10 so as to produce the cantilever beam vibration absorber natural frequency $\omega_{nat.CB}$ desired, utilizing the lowest numerical mode of vibration which will produce this desired $\omega_{nat.CB}$.

For a more complete explanation of the mathematics discussed herein, reference may be made to the texts "Theory of Vibration with Application" by William T. Thomson or "Formulas for Stress and Strain" by Raymond J. Roark.

Figure 11:
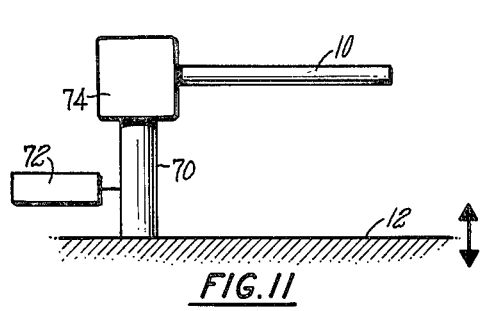
FIGS. 11 and 12 are showings of my vibration controller demonstrating means for applying driving forces to the cantilever beam base so as to apply a vibration exciting force thereto and hence to the cantilever beam.
Figure 12:
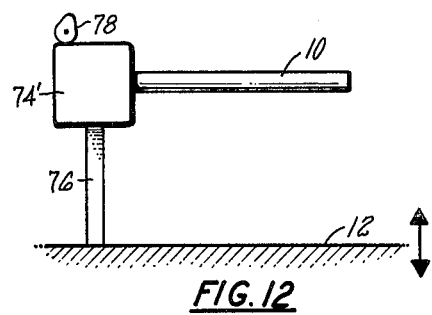

While I have shown my vibration absorber 10 as being fixedly, i.e. directly, mounted to the vibration prone structure 12 in my FIG. 1 embodiment, my preferred embodiment, and while I have described my invention in relation to utilizing the vibration absorber 10 to damp vibrations, my cantilever beam vibration controller 10 described herein also has the capability of being used to excite certain modes of vibration when used as shown in my FIG. 11 and 12 embodiments.

In the FIG. 11 embodiment, my cantilever beam vibration absorber 10 is mounted from vibration prone structure 12 through hydraulic piston-cylinder arrangement 70 which can be actuated in known fashion by servo 72 to impart selected vibrations to support 74 and hence to cantilever beam vibration controller 10.

In FIG. 12, the vibration absorber support 74' is supported from vibration prone structure 12 by flexible member 76. Cam 78 is selectively shaped and selectively rotated so as to impart selected vibratory motion to support 74 and hence to vibration controller 10, thereby providing excitation to the system, rather than damping.

Figure 13:
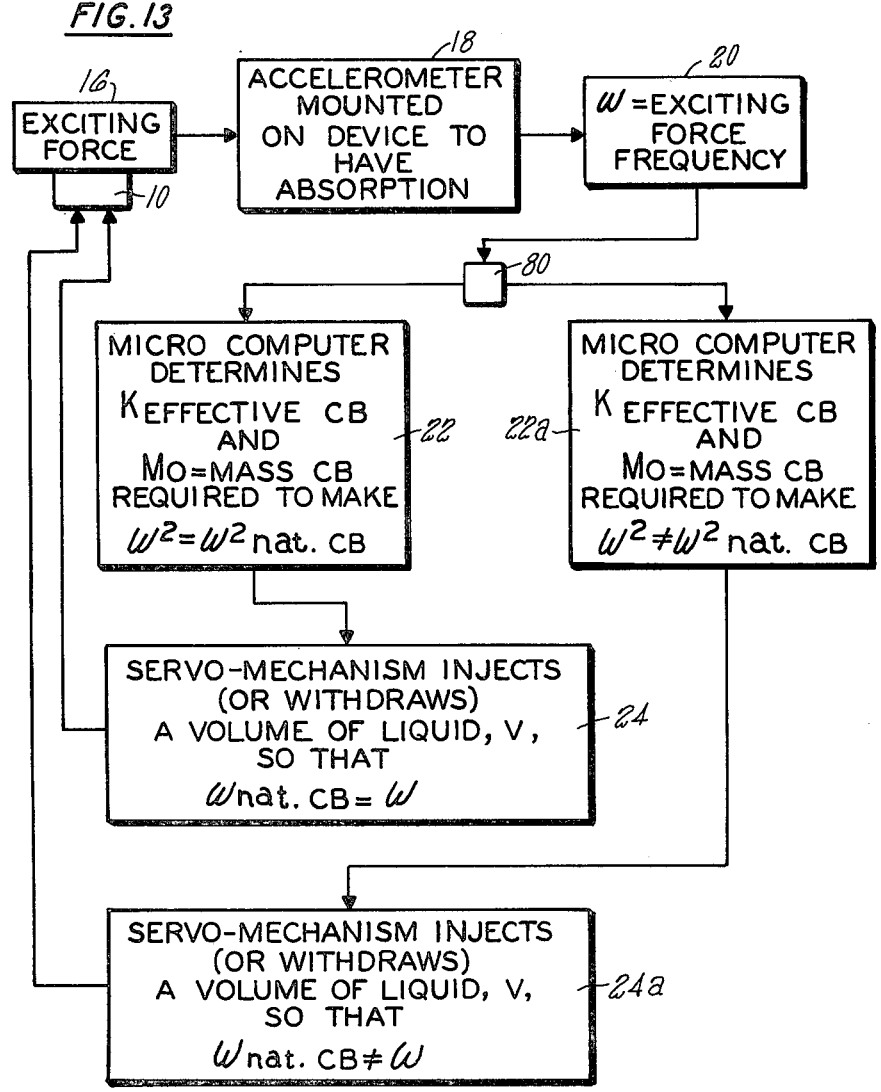
FIG. 13 is similar to FIG. 2 except that the natural frequency of cantilever beam can be made equal to or selectively dissimilar to the natural frequency of the vibration prone system.

FIG. 13 shows another mode of operation of my cantilever beam mechanism 10 in which it is used either to damp vibrations or excite selected vibrations in mechanism 16. It will be noted that FIG. 13 is similar to FIG. 2 but with provisions added to permit the cantilever beam 10 to excite vibrations rather than damp vibrations. Reference numerals used for similar apparatus in FIG. 2 are also used in FIG. 13 and elements 16–24 operate in the FIG. 13 arrangement precisely as described in connection with the FIG. 2 arrangement and are used when the pilot selects to utilize cantilever beam 10 as a vibration absorber or damper. When the pilot selects to use cantilever beam 10 as a vibration excitation mechanism, he energizes switch 80 which causes the signal from element 20 to go to microcomputer 22a rather than microcomputer 22. The signal generated by microcomputer 22a is as indicated in FIG. 13, namely to establish the natural frequency of the cantilever beam to be different from the natural frequency of the vibration prone structure 16. This "different from" frequency signal from computer 22a is transmitted to servomechanism 24a, which functions to inject or withdraw a selected volume of liquid, V, into cantilever beam vibration absorber 10 so as to selectively establish the natural frequency of the cantilever beam to be dissimilar to the natural frequency of the vibration prone structure 16, thereby causing the cantilever beam to function to establish a vibration excitation force on the vibration prone structure 16 so as to selectively vary its vibration characteristics. Those skilled in the art will recognize that the excitation of an additional vibrational force within a system can serve to reduce vibrations since the vibrations generated by the second vibratory exciting force from 10 and the natural frequency of vibration prone structure 16 can be made to be cancelling.

My FIGS. 11 and 12 vibration excitation modifications may be used in combination with my FIG. 2 or FIG. 13 embodiment. To best understand the cooperation between these embodiments, it is best to consider the following equation:

$$F_b(t) = M_o \ddot{Y}_b \qquad \text{Eq. 11}$$

where $F_b$ = the exciting force 16 and the driving force imposed by either the servo operated piston-cylinder mechanism 70 of FIG. 11 or cam 78 of FIG. 12, where $M_o$ is the total mass of cantilever beam 10 including the weight of the cantilever beam and the weight of the fluid therein, and $\ddot{}_b$ is the acceleration of the cantilever beam base 74 or 74'.

Considering Equation 11, it will be noted that the acceleration of the cantilever beam base 74, 74' can be changed by selectively varying $M_o$ or $F_b$. $M_o$ is changed as shown in the FIGS. 1 and 13 embodiment by varying the amount of liquid injected into or withdrawn from cantilever beam 10. $F_b$ can be changed through the action of piston-cylinder mechanism 70 actuated by servo 72 or by the action of cam 78.

It will therefore be seen that the frequency generated in cantilever beam 10 can be varied when the FIG. 11 or 12 embodiments are used in combination with the FIG. 2 or 13 embodiments by either using the mechanism of FIG. 2 to cause cantilever beam 10 to vibrate so as to reduce or eliminate the vibrations of the vibration prone system, by utilizing the FIG. 13 construction, and, in particular, the 22a microcomputer and 24a servo mechanism portion thereof to vary $M_o$ so that the natural frequency of the cantilever beam vibrator is different from the natural frequency of the vibration prone system to thereby apply vibration excitation to the vibration prone system. At the same time, either the FIG. 11 or FIG. 12 embodiments can be used with the FIG. 2 or FIG. 13 embodiments to add a second driving force to exciting force 16 through the action of element 70–72 of FIG. 11 or 78 of FIG. 12 to vary the quantity $F_b$ in the FIG. 11 equation and hence the mode of vibration of cantilever beam 10 by adding an excitation force thereto by means of the FIG. 11 or 12 mechanism.

I wish it to be understood that I do not desire to be limited to the exact details of construction shown and described, for obvious modifications will occur to a person skilled in the art.

I claim:

1. A multi-frequency vibration controller comprising: a vibration prone structure, a cantilever beam of selected natural frequency connected to the vibration prone structure so as to vibrate therewith and having a hollow port into which fluid may be added or withdrawn to vary the cantilever beam total mass and natural frequency, means operatively connected to the vibration prone structure to continuously determine the present vibrating frequency of the vibration prone structure and to generate a first signal representative thereof, means responsive to said first signal and operable to determine the optimum total mass of the cantilever beam required to cause the cantilever beam natural frequency to be equal to or selectively unequal to the frequency of the present vibrations of the vibration prone structure so determined, and to generate a second signal representative thereof, and means responseve to said second signal and operable to selectively introduce or withdraw fluid to or from the hollow portion of the cantilever beam to produce said optimum cantilever beam total mass and hence natural frequency to be equal to or selectively unequal to the frequency of the present vibrations of the vibration prone structure to thereby control the vibrations of the vibration prone structure.

2. A vibration controller according to claim 1 wherein said cantilever beam is cylindrical in shape and wherein said hollow portion of said cantilever beam comprises at least one hollow passage extending parallel to the cantilever beam axis.

3. A vibration controller according to claim 1 wherein said hollow portion of said cantilever beam comprises a plurality of hollow cylindrical passages extending parallel to the cantilever beam axis.

4. A vibration controller according to claim 3 wherein said fluid introducing or withdrawing means comprises servo means operative to selectively introduce or withdraw fluid into one or more of the cantilever beam's axially extending interior hollow passages so that each such passage is either completely full or completely empty of fluid to thereby produce the desired cantilever beam total mass.

5. A vibration controller according to claim 4 wherein said vibrating frequency determining means is an accelerometer fixedly positioned on the vibration prone structure to vibrate therewith and to accurately reflect the frequency of vibration thereof at all times.

6. A vibration controller according to claim 5 wherein said cantilever beam total mass determining means is a microcomputer operatively connected to receive vibrating frequency signals from said accelerometer and to provide control signals to said servo means 7. A vibration controller according to claim 6 wherein said microcomputer is programmed to selectively inject or withdraw fluid from said cantilever beam interior hollow passages to vary the total mass of the cantilever beam so that the cantilever beam natural frequency is equal to the present frequency of vibration of the vibration prone structure under control utilizing the following equation:

$$\omega_{nat.CB} = \beta_n^2 \, EI/m_o,$$

where $\omega_{nat.CB}$ is the cantilever beam natural frequency, $\beta_n$ is an international constant, E is the modulus of elasticity of the cantilever beam, I is the cross-sectional area moment of inertia of the cantilever beam, and $m_o$ is the distributive mass, i.e., mass per unit length of the cantilever beam with a selected mass or volume of fluid therein.

8. A vibration controller according to claim 6 wherein said microcomputer is programmed to control said servo means to produce the optimum array of filled and/or emptied interior hollow passages to produce the lowest numerical mode of vibration of the cantilever beam to result in a natural frequency of the vibration absorber equal to the frequency of vibration of the vibration prone structure under control.

9. A vibration controller according to claim 8 wherein said servo means is operative to introduce or withdraw more than one fluid to said interior hollow passages.

10. A vibration controller according to claim 6 wherein said microcomputer is programmed to introduce or withdraw a desired volume and hence mass of fluid into said interior hollow passages as required to establish the cantilever beam natural frequency equal to the present vibrating frequency of the vibration prone structure under control.

11. A vibration controller according to claim 6 wherein said hollow passages in said cantilever beam are selectively positioned to optimally tune the vibration controller.

12. A vibration controller according to claim 1 and further including means to apply a vibration exciting force to said cantilever beam.

13. A vibration controller according to claim 12 wherein said cantilever beam is supported from said vibration prone structure by means of a fluid actuated cylinderpiston mechanism and including means to selectively cause the piston to move within the cylinder to impose a vibration exciting force on said cantilever beam.

14. A vibration controller according to claim 12 and including flexible means to support said cantilever beam from said vibration prone structure and further including means to impose a vibration exciting force on said flexible means and hence said cantilever beam.

15. A vibration controller according to claim 14 wherein said force imposing means is a selectively rotating cam.

* * * * *

UNITED STATES PATENT AND TRADEMARK OFFICE
CERTIFICATE OF CORRECTION

PATENT NO. : 4,470,121        Page 1 of 2
DATED     : September 4, 1984
INVENTOR(S) : FREDERICK J. EBERT It is certified that error appears in the above-identified patent and that said Letters Patent is hereby corrected as shown below:

|  |  |  |
|---|---|---|
|  | Line 18 | "$\beta\ 1$" should read --$\beta\ \ell$-- |
|  | Line 20 | "1" should read --$\ell$-- |
|  | Line 31 | "1" should read --$\ell$-- |
|  | Line 33 | "1" should read --$\ell$-- |
| Col. 6, | Line 18 | "EI 1" should read --EI $\ell$-- |
|  | Line 30 | "$(\beta_n\ 1)^2$" should read --$(\beta_n\ \ell)^2$-- |
|  | Line 30 | "$(\beta_n\ 1)$" should read --$(\beta_n\ \ell)$-- |
|  | Line 44 | "1" should read --$\ell$-- |
|  | Line 48 | After "mode", insert --of-- |
|  | Line 55 | "1" should read --$\ell$-- |
|  | Line 59 | "1" should read --$\ell$-- |
|  | Line 60 | "1" should read --$\ell$-- |
| Col. 5, | Line 14 | "COSH ($\beta$ 1)COS($\beta$ 1)= -1" should read --COSH ($\beta\ \ell$)COS($\beta\ \ell$) = -1,-- |
|  | Line 16 | "$\beta$ 1" should read --$\beta\ \ell$-- |
|  | Line 18 | "1" should read --$\ell$-- |

UNITED STATES PATENT AND TRADEMARK OFFICE
CERTIFICATE OF CORRECTION

PATENT NO. : 4,470,121

DATED : September 4, 1984

INVENTOR(S) : FREDERICK J. EBERT

It is certified that error appears in the above-identified patent and that said Letters Patent is hereby corrected as shown below:

Col. 10, Line 32   "b" should read --$\ddot{Y}_b$--

Col. 11, Line 3   "port" should read --portion--

Signed and Sealed this

Third Day of December 1985

[SEAL]

Attest:

DONALD J. QUIGG

*Attesting Officer*   *Commissioner of Patents and Trademarks*